(12) United States Patent
Netzel et al.

(10) Patent No.: US 10,987,124 B2
(45) Date of Patent: Apr. 27, 2021

(54) SURGICAL INSTRUMENTS AND JAW MEMBERS THEREOF

(71) Applicant: COVIDIEN LP, Mansfield, MA (US)

(72) Inventors: Kenneth E. Netzel, Loveland, CO (US); Jason L. Craig, Loveland, CO (US)

(73) Assignee: Covidien LP, Mansfield, MA (US)

( * ) Notice: Subject to any disclaimer, the term of this patent is extended or adjusted under 35 U.S.C. 154(b) by 442 days.

(21) Appl. No.: 15/800,833

(22) Filed: Nov. 1, 2017

(65) Prior Publication Data

US 2018/0140352 A1 May 24, 2018

Related U.S. Application Data

(60) Provisional application No. 62/425,314, filed on Nov. 22, 2016.

(51) Int. Cl.
*A61B 17/28* (2006.01)
*A61B 17/32* (2006.01)
*A61B 18/00* (2006.01)

(52) U.S. Cl.
CPC ......... *A61B 17/320092* (2013.01); *A61B 2017/2825* (2013.01); *A61B 2017/2829* (2013.01); *A61B 2017/320069* (2017.08); *A61B 2017/320094* (2017.08); *A61B 2018/0019* (2013.01)

(58) Field of Classification Search
CPC .......... A61B 17/320092; A61B 2017/320094; A61B 2017/2825; A61B 2017/2829; A61B 2018/0019; A61B 18/1445
See application file for complete search history.

(56) References Cited

U.S. PATENT DOCUMENTS

| | | |
|---|---|---|
| 3,469,211 A | 9/1969 | Shoh |
| 4,277,710 A | 7/1981 | Harwood et al. |
| 4,587,958 A | 5/1986 | Noguchi et al. |
| 4,827,911 A | 5/1989 | Broadwin et al. |
| 4,922,902 A | 5/1990 | Wuchinich et al. |
| 4,965,532 A | 10/1990 | Sakurai |
| 4,973,876 A | 11/1990 | Roberts |
| 5,014,407 A | 5/1991 | Boughten et al. |
| 5,180,363 A | 1/1993 | Idemoto et al. |
| 5,216,338 A | 6/1993 | Wilson |
| 5,330,502 A | 7/1994 | Hassler et al. |

(Continued)

FOREIGN PATENT DOCUMENTS

| | | |
|---|---|---|
| EP | 1518505 A1 | 3/2005 |
| EP | 3207884 A1 | 8/2017 |

(Continued)

OTHER PUBLICATIONS

European Search Report dated Feb. 2, 2018, corresponding to European Application No. 17202686.6; 9 pages.

(Continued)

*Primary Examiner* — Michael F Peffley
*Assistant Examiner* — Bo Ouyang

(57) ABSTRACT

A jaw member for use with a surgical instrument includes a support base, a jaw liner, and an elongated plate. The support base defines a cavity therein configured for receipt of the jaw liner. The elongated plate is configured to be seated in the cavity of the support base adjacent the jaw liner to secure the jaw liner relative to the support base.

20 Claims, 11 Drawing Sheets

(56) References Cited

U.S. PATENT DOCUMENTS

| | | | |
|---|---|---|---|
| 5,421,829 A | 6/1995 | Olichney et al. | |
| 5,456,684 A | 10/1995 | Schmidt et al. | |
| 5,532,539 A | 7/1996 | Hielscher | |
| 5,562,682 A | 10/1996 | Oberlin et al. | |
| 5,634,466 A | 6/1997 | Gruner | |
| 5,637,947 A | 6/1997 | Kising et al. | |
| 5,649,957 A | 7/1997 | Levin | |
| 5,700,952 A | 12/1997 | Andersen | |
| 5,702,408 A | 12/1997 | Wales et al. | |
| 5,704,534 A | 1/1998 | Huitema et al. | |
| 5,797,537 A | 8/1998 | Oberlin et al. | |
| 5,816,476 A | 10/1998 | Buice et al. | |
| 5,817,119 A | 10/1998 | Klieman et al. | |
| 5,897,523 A | 4/1999 | Wright et al. | |
| 6,063,098 A | 5/2000 | Houser et al. | |
| 6,068,647 A | 5/2000 | Witt et al. | |
| 6,129,735 A * | 10/2000 | Okada | A61B 17/320068 606/169 |
| 6,163,100 A | 12/2000 | Morizaki et al. | |
| 6,193,709 B1 | 2/2001 | Miyawaki et al. | |
| 6,241,139 B1 | 6/2001 | Milliman et al. | |
| 6,320,298 B1 | 11/2001 | Kawabe | |
| 6,454,782 B1 | 9/2002 | Schwemberger | |
| 6,480,796 B2 | 11/2002 | Wiener | |
| 6,569,109 B2 | 5/2003 | Sakurai et al. | |
| 6,588,277 B2 | 7/2003 | Giordano et al. | |
| 6,626,926 B2 | 9/2003 | Friedman et al. | |
| 6,652,547 B2 | 11/2003 | Rabiner et al. | |
| 6,663,641 B1 | 12/2003 | Kovac et al. | |
| 6,666,854 B1 | 12/2003 | Lange | |
| 6,678,621 B2 | 1/2004 | Wiener et al. | |
| 6,679,899 B2 | 1/2004 | Wiener et al. | |
| 6,752,815 B2 | 6/2004 | Beaupre | |
| 6,761,690 B2 | 7/2004 | Sakurai et al. | |
| 6,887,252 B1 | 5/2005 | Okada et al. | |
| 6,898,536 B2 | 5/2005 | Wiener et al. | |
| 6,958,070 B2 | 10/2005 | Witt et al. | |
| 6,984,919 B2 | 1/2006 | Iino et al. | |
| 7,179,271 B2 | 2/2007 | Friedman et al. | |
| 7,247,141 B2 | 7/2007 | Makin et al. | |
| 7,270,646 B2 | 9/2007 | Sakurai et al. | |
| 7,273,483 B2 | 9/2007 | Wiener et al. | |
| 7,475,801 B2 | 1/2009 | Johansen et al. | |
| 7,481,824 B2 | 1/2009 | Boudreaux et al. | |
| 7,482,888 B1 | 1/2009 | Kleveland | |
| 7,503,895 B2 | 3/2009 | Rabiner et al. | |
| 7,513,160 B2 | 4/2009 | Lynch et al. | |
| 7,514,844 B2 | 4/2009 | Unkrich | |
| 7,528,670 B2 | 5/2009 | Soh | |
| 7,544,200 B2 | 6/2009 | Houser | |
| 7,566,334 B2 | 7/2009 | Christian et al. | |
| 7,614,878 B2 | 11/2009 | Paschke et al. | |
| 8,002,782 B2 | 8/2011 | Witt et al. | |
| 8,057,467 B2 | 11/2011 | Faller et al. | |
| 8,197,633 B2 * | 6/2012 | Guerra | A61B 18/1445 156/314 |
| 8,292,888 B2 | 10/2012 | Whitman | |
| 8,366,727 B2 | 2/2013 | Witt et al. | |
| 8,444,664 B2 | 5/2013 | Balanev et al. | |
| 8,469,982 B2 | 6/2013 | Witt et al. | |
| 8,518,067 B2 | 8/2013 | Masuda et al. | |
| 8,523,890 B2 | 9/2013 | Whitman | |
| 8,535,340 B2 | 9/2013 | Allen | |
| 8,672,959 B2 | 3/2014 | Witt et al. | |
| 8,715,306 B2 | 5/2014 | Faller et al. | |
| 9,044,261 B2 | 6/2015 | Houser | |
| 9,414,853 B2 | 8/2016 | Stulen et al. | |
| 9,439,670 B2 | 9/2016 | Witt et al. | |
| 9,724,120 B2 | 8/2017 | Faller et al. | |
| 2002/0002380 A1 | 1/2002 | Bishop | |
| 2002/0111622 A1 | 8/2002 | Khandkar et al. | |
| 2004/0097911 A1 | 5/2004 | Murakami et al. | |
| 2005/0027311 A1 | 2/2005 | Wiener et al. | |
| 2005/0049546 A1* | 3/2005 | Messerly | A61B 17/320092 604/22 |
| 2005/0070800 A1 | 3/2005 | Takahashi | |
| 2005/0143769 A1 | 6/2005 | White et al. | |
| 2005/0192610 A1 | 9/2005 | Houser et al. | |
| 2006/0100646 A1 | 5/2006 | Hart et al. | |
| 2006/0190031 A1 | 8/2006 | Wales et al. | |
| 2007/0179526 A1 | 8/2007 | Hart et al. | |
| 2007/0282332 A1 | 12/2007 | Witt et al. | |
| 2008/0188877 A1 | 8/2008 | Hickingbotham | |
| 2008/0234711 A1 | 9/2008 | Houser et al. | |
| 2008/0277447 A1 | 11/2008 | Smith et al. | |
| 2008/0294191 A1 | 11/2008 | Lee | |
| 2008/0308607 A1 | 12/2008 | Timm et al. | |
| 2009/0030311 A1 | 1/2009 | Stulen et al. | |
| 2009/0030439 A1 | 1/2009 | Stulen | |
| 2009/0036913 A1 | 2/2009 | Wiener et al. | |
| 2009/0036914 A1 | 2/2009 | Houser | |
| 2009/0065549 A1 | 3/2009 | Viola | |
| 2009/0069842 A1 | 3/2009 | Lee et al. | |
| 2009/0076534 A1 | 3/2009 | Shelton, IV et al. | |
| 2009/0118751 A1 | 5/2009 | Wiener et al. | |
| 2009/0131962 A2 | 5/2009 | Houser et al. | |
| 2009/0143797 A1 | 6/2009 | Smith et al. | |
| 2009/0143800 A1 | 6/2009 | Deville et al. | |
| 2009/0143806 A1 | 6/2009 | Witt et al. | |
| 2009/0182365 A1 | 7/2009 | Cuny | |
| 2009/0187185 A1 | 7/2009 | Lyons et al. | |
| 2009/0198272 A1 | 8/2009 | Kerver et al. | |
| 2009/0264909 A1 | 10/2009 | Beaupre | |
| 2010/0030248 A1 | 2/2010 | Palmer et al. | |
| 2010/0179545 A1 | 7/2010 | Twomey et al. | |
| 2012/0296356 A1 | 11/2012 | Balanev et al. | |
| 2012/0310229 A1 | 12/2012 | Gregg | |
| 2013/0030328 A1 | 1/2013 | Dycus et al. | |
| 2013/0085419 A1 | 4/2013 | Stoddard et al. | |
| 2013/0121366 A1 | 5/2013 | Misuchenko et al. | |
| 2013/0197511 A1 | 8/2013 | Balanev et al. | |
| 2013/0325047 A1 | 12/2013 | Craig | |
| 2015/0148832 A1 | 5/2015 | Boudreaux et al. | |
| 2015/0297255 A1 | 10/2015 | Fan et al. | |
| 2017/0238959 A1 | 8/2017 | Craig et al. | |
| 2017/0312016 A1* | 11/2017 | Strobl | A61B 18/1482 |

FOREIGN PATENT DOCUMENTS

| | | |
|---|---|---|
| JP | 2008515562 A | 5/2008 |
| JP | 2009514566 A | 4/2009 |
| WO | 2006042210 A2 | 4/2006 |
| WO | 2011/008672 A2 | 1/2011 |
| WO | 2012/061645 A1 | 5/2012 |
| WO | 2015/137139 A1 | 9/2015 |

OTHER PUBLICATIONS

Japanese Office Action (with English translation), dated Sep. 27, 2018, corresponding to Japanese Application No. 2017-223496; 19 total pages.

European Search Report for EP 12763063 dated Mar. 11, 2015.

Supplementary European Search Report for EP 12763063 dated Jul. 1, 2015.

PCT Search Report from International Application No. PCT/US2012/031601, dated Jul. 23, 2012.

\* cited by examiner

SURGICAL INSTRUMENTS AND JAW MEMBERS THEREOF

CROSS REFERENCE TO RELATED APPLICATION

The present application claims the benefit of and priority to U.S. Provisional Application Ser. No. 62/425,314, filed on Nov. 22, 2016 the entire contents of which are incorporated herein by reference.

BACKGROUND

Technical Field

The present disclosure relates to jaw members of surgical instruments and, more particularly, to jaw members of ultrasonic surgical instruments.

Background of Related Art

Some surgical instruments have an end effector including at least one jaw member configured to treat or manipulate tissue of a patient. An example of such a surgical instrument is an ultrasonic surgical instrument that utilizes ultrasonic energy, i.e., ultrasonic vibrations, to treat tissue. More specifically, an ultrasonic surgical instrument that utilizes mechanical vibration energy transmitted at ultrasonic frequencies to coagulate, cauterize, fuse, seal, cut, desiccate, fulgurate, or otherwise treat tissue. Such an ultrasonic surgical instrument is configured to transmit ultrasonic energy produced by a generator and transducer assembly along a waveguide to an end effector that is spaced-apart from the generator and transducer assembly. The end effector includes a blade and a jaw member configured to clamp and treat tissue between the blade and the jaw member.

Typically, the vibrations induced in the blade will be transferred to the jaw member, which may damage the jaw member or other components of the surgical instrument. Additionally, the high frequency vibrations may generate high temperatures in the jaw member, which may also damage the jaw member.

Accordingly, a need exists for an improved jaw member constructed to withstand the high frequency vibrations generated by the ultrasonic surgical instrument and/or to withstand the high temperatures produced thereby. Further, a need exists to provide such a jaw member that is efficient and not overly difficult or expensive to manufacture.

SUMMARY

In one aspect of the present disclosure, an embodiment of a jaw member for use with a surgical instrument is provided. The jaw member includes a support base, a jaw liner, and an elongated body. The support base has a proximal portion configured to be pivotably coupled to a surgical instrument, and a distal portion. The support base defines a cavity therein that extends longitudinally between the proximal and distal portions. The support base includes a stepped portion formed therein, which defines a first ledge and a second ledge. The jaw liner includes an elongate body configured for receipt in the cavity of the support base, and a projection extending radially outward from a periphery of the elongate body. The projection is configured to be seated on the first ledge of the support base. The elongated plate is configured to be seated on the second ledge of the support base adjacent the jaw liner to secure the jaw liner relative to the support base.

In some embodiments, the stepped portion may be disposed on both sides of the cavity of the support base and extend longitudinally therealong.

It is contemplated that the support base may include a first side wall defining a first side of the cavity and a second side wall defining a second side of the cavity. Each of the first and second ledges of the support base may protrude laterally from the first and second side walls inwardly into the cavity.

It is envisioned that the first ledge may protrude a first distance laterally from the first and second side walls and the second ledge may protrude a second distance laterally from the first and second side walls. The first distance is greater than the second distance.

In some embodiments, each of the first and second ledges of the support base may extend along a length of the support base.

It is contemplated that the support base may have an outer surface that extends over the second ledge such that the plate is configured to be captured between the outer surface of the support base and the second ledge of the support base.

It is envisioned that the jaw liner may have a tissue-contacting surface formed on the elongate body of the jaw liner. The tissue-contacting surface of the jaw liner may be fabricated from plastic, for example, polytetrafluoroethylene, polyetheretherketone, perfluoroalkoxy, and/or fluorinated ethylene propylene. The tissue-contacting surface may have a plurality of teeth disposed along a length of the jaw liner. The support base may have an inner surface, and the tissue-contacting surface of the jaw liner may project from the inner surface of the support base.

In some embodiments, the plate may have a proximal portion and a tab extending from the proximal portion. The tab of the plate may be configured to abut a proximal portion of the projection of the jaw liner to prevent proximal movement of the jaw liner relative to the support base.

It is contemplated that the cavity of the support base may be closed via a bridge inhibiting slidable insertion of the jaw liner into the cavity while permitting slidable insertion of the elongated plate into the cavity.

It is envisioned that the cavity of the support base may have a closed proximal end such that proximal movement of the jaw liner relative to the support base is inhibited.

In yet another aspect of the present disclosure, a surgical instrument is provided and includes a handle assembly, an elongated body portion extending distally from the handle assembly, and a tool assembly operably coupled to the elongated body portion. The tool assembly includes a blade member and a jaw member. The jaw member includes a support base, a jaw liner, and an elongated plate. The support base has a proximal portion pivotably coupled to the elongated body portion, and a distal portion. The support base defines a cavity therein that extends longitudinally between the proximal and distal portions. The support base includes a stepped portion formed therein, which defines a first ledge and a second ledge. The jaw liner includes an elongate body received in the cavity of the support base and a projection extending radially outward from a periphery of the elongate body and seated on the first ledge of the support base. The elongated plate is seated on the second ledge of the support base adjacent the jaw liner to secure the jaw liner relative to the support base. The jaw member is movable relative to the blade member between an open position, in which the jaw liner of the jaw member is spaced from the blade member, and a closed position, in which the jaw liner of the jaw member is approximated relative to the blade member.

Further details and aspects of exemplary embodiments of the present disclosure are described in more detail below with reference to the appended figures.

As used herein, the terms parallel and perpendicular are understood to include relative configurations that are substantially parallel and substantially perpendicular up to about + or −10 degrees from true parallel and true perpendicular.

BRIEF DESCRIPTION OF THE DRAWINGS

The above and other aspects and features of the present disclosure will become more apparent in view of the following detailed description when taken in conjunction with the accompanying drawings, wherein.

DETAILED DESCRIPTION

Figure 1A:
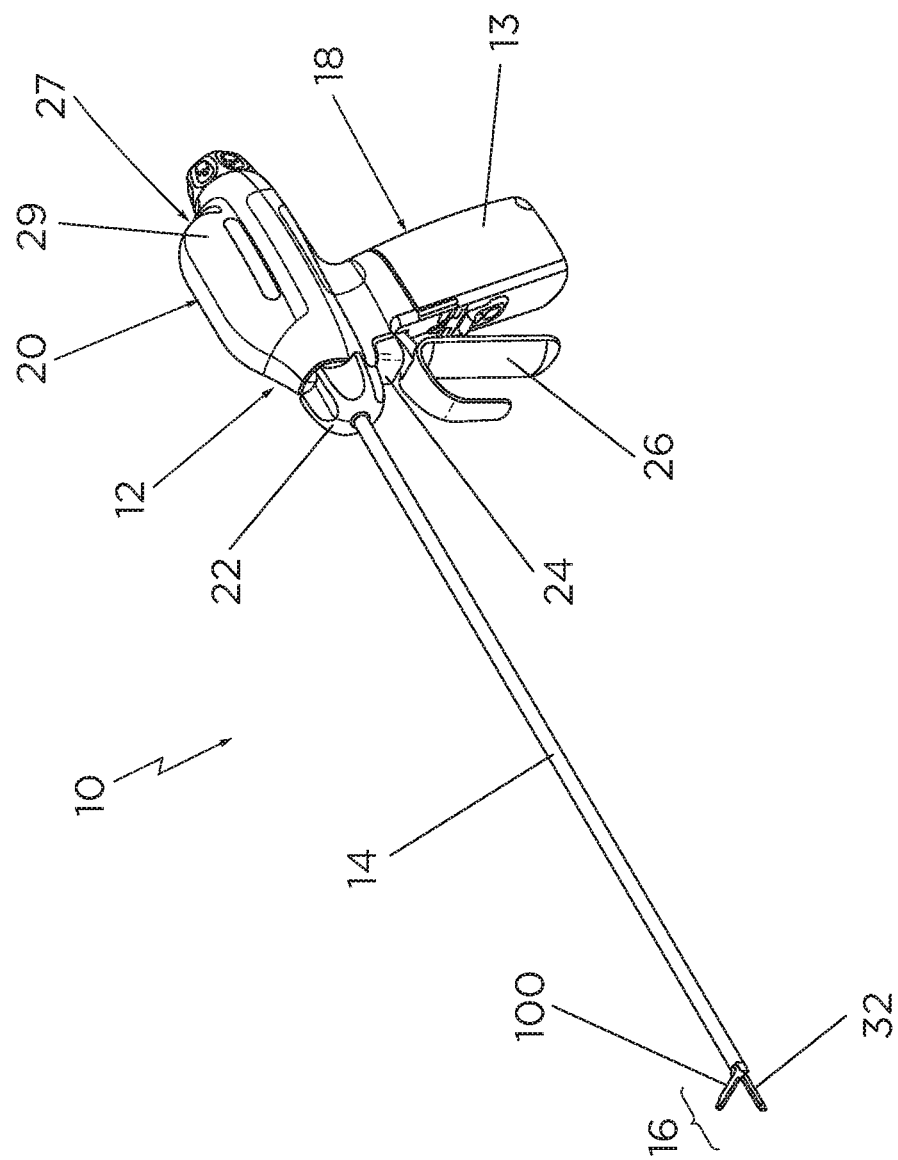
FIG. 1A is a perspective view of an illustrative embodiment of an ultrasonic surgical instrument provided in accordance with the present disclosure, including a tool assembly thereof illustrated in an open condition.

Embodiments of the presently disclosed jaw members, surgical instruments including such jaw members, and methods of manufacturing thereof, are described in detail with reference to the drawings, in which like reference numerals designate identical or corresponding elements in each of the several views. As used herein the term "distal" refers to that portion of the surgical instrument and/or jaw member thereof, that is closer to the patient, while the term "proximal" refers to that portion of the surgical instrument and/or jaw member, that is farther from the patient.

Figure 1B:
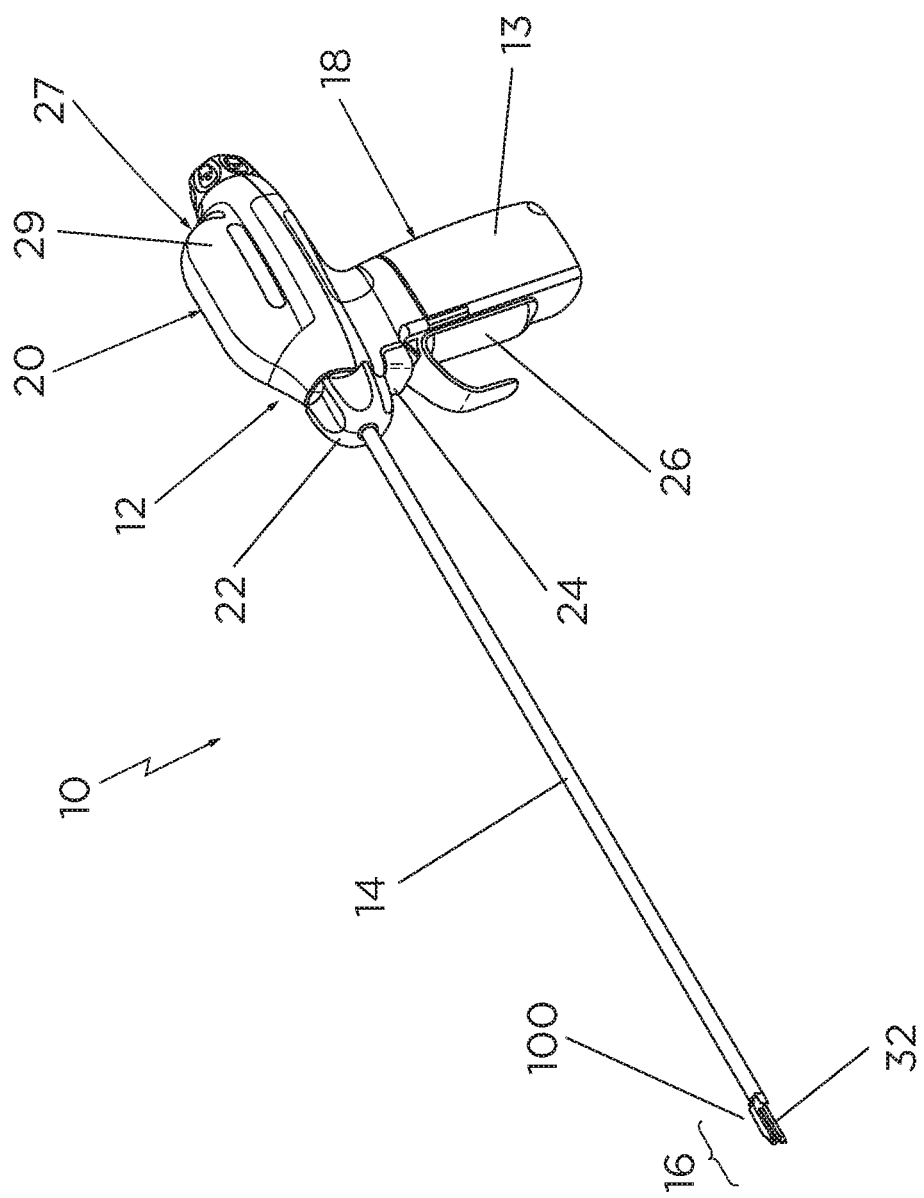
FIG. 1B is a perspective view of the ultrasonic surgical instrument of FIG. 1A, wherein the tool assembly is illustrated in a closed, clamping condition.
Figure 2:
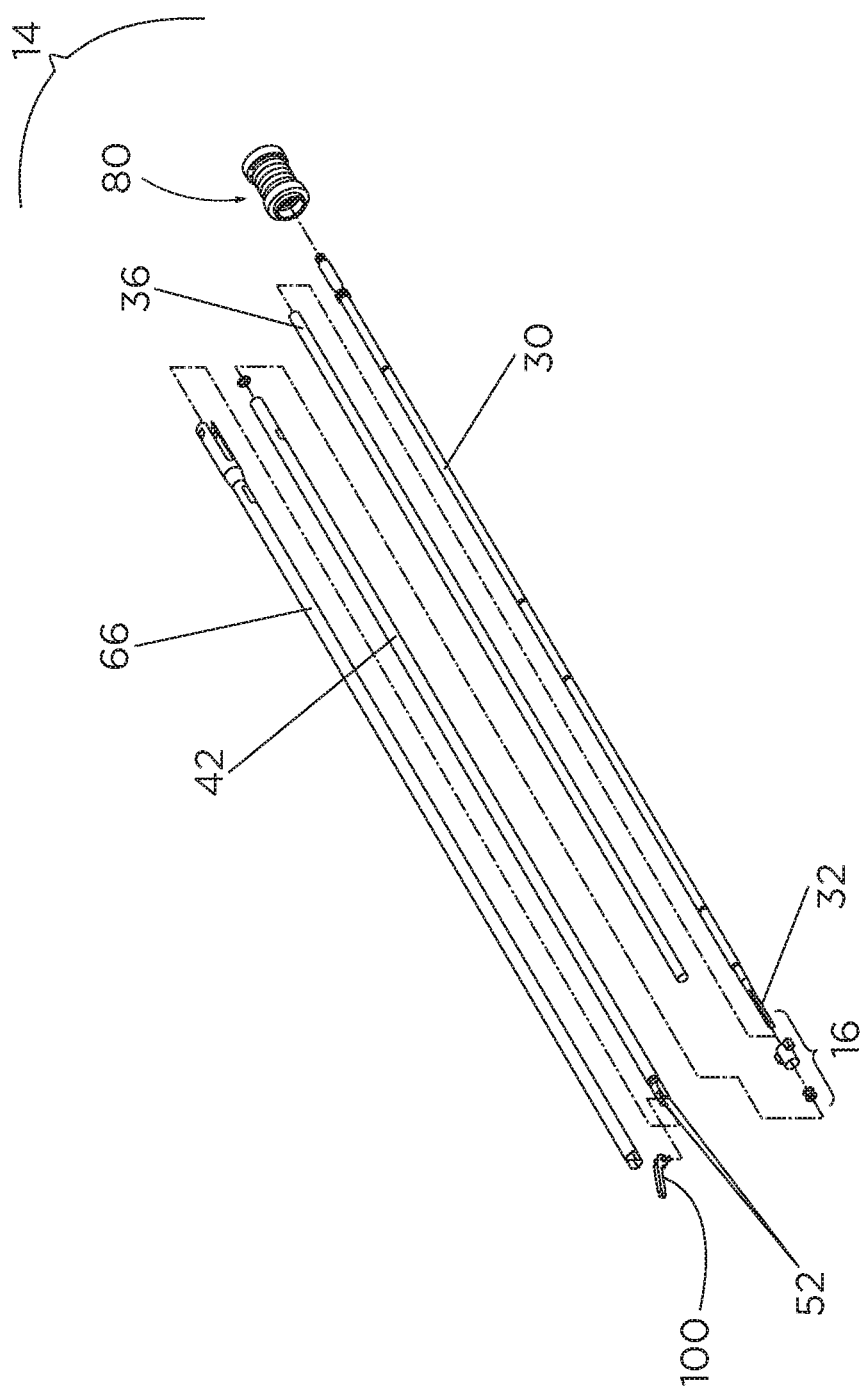
FIG. 2 is an exploded, perspective view of a shaft, a waveguide, and the tool assembly of the ultrasonic surgical instrument of FIG. 1A.

For purposes of illustration only, the following detailed description of a surgical instrument will be limited to describing unique jaw members as incorporated on an embodiment of an ultrasonic surgical instrument 10 as shown generally in FIGS. 1A, 1B, and 2. The jaw members include a jaw support base and a jaw liner fixed within the jaw support base by an elongated plate that inhibits detachment of the jaw liner from the jaw support base during use of ultrasonic surgical instrument 10. It is contemplated that the various jaw members detailed herein may also be used with other surgical instruments other than ultrasonic surgical instrument 10, for example, any suitable type of surgical instrument that functions to clamp and/or treat tissue, such as any suitable electromechanical surgical instrument or electrosurgical instrument.

Ultrasonic surgical instrument 10 generally includes a handle assembly 12, an elongated body portion 14, and a tool assembly 16. Tool assembly 16 includes a blade member 32 and a clamp member or jaw member 100. Handle assembly 12 supports a battery assembly 18 and an ultrasonic transducer and generator assembly ("TAG") 20, and includes a rotatable nozzle 22, an activation button 24, and a clamp trigger 26. Battery assembly 18 and TAG 20 are each releasably secured to handle assembly 12 to facilitate disposal of the entire device, with the exception of battery assembly 18 and TAG 20. However, it is contemplated that any or all of the components of ultrasonic surgical instrument 10 may be configured as disposable single-use components or sterilizable multi-use components.

Elongated body portion 14 of ultrasonic surgical instrument 10 includes a waveguide 30 which extends distally from handle assembly 12 to tool assembly 16. A distal portion of waveguide 30 defines blade member 32 of tool assembly 16. A proximal portion of waveguide 30 is configured to engage TAG 20. Elongated body portion 14 of ultrasonic surgical instrument 10 further includes an isolation tube 36 positioned about waveguide 30 to prevent the transfer of ultrasonic energy from waveguide 30 to an inner support tube 42 of elongated body portion 14. Waveguide 30 and inner support tube 42 are rotatably coupled to rotatable nozzle 22 such that rotation of nozzle 22 effects corresponding rotation of inner support tube 42 and waveguide 30. Elongated body portion 14 further includes an actuator tube 66 coupled to inner support tube 42 and configured to rotate upon rotation of nozzle 22.

Inner support tube 42 of elongated body portion 14 is positioned about isolation tube 36 and includes a distal end having a pair of spaced clamp support arms 52. Spaced clamp support arms 52 are configured to pivotally engage pivot members 114 (FIG. 3) formed on jaw member 100 of tool assembly 16 to enable pivoting of jaw member 100 between an open position (FIG. 1A), in which jaw member 100 is spaced from blade member 32, and a closed position (FIG. 1B), in which jaw member 100 is approximated relative to blade member 32. Jaw member 100 is moved between the open and closed positions in response to actuation of clamp trigger 26, as detailed below.

Outer actuator tube 66 of elongated body portion 14 is slidably supported about inner support tube 42 (although actuator tube 66 may alternatively be slidably disposed within support tube 42) and is operably coupled to jaw member 100 such that jaw member 100 is pivoted from the open position (FIG. 1A) to the closed position (FIG. 1B) as actuator tube 66 is slid about inner support tube 42. Actuator tube 66 is operably coupled with rotatable nozzle 22 such that outer actuator tube 66 is rotatably secured to, and slidable relative to, rotatable nozzle 22. Further, a proximal portion of outer actuator tube 66 is operably coupled with a drive mechanism 80 of handle assembly 12, as detailed below.

Handle assembly 12 includes drive mechanism 80 supported therein for linear movement relative to handle assembly 12. Handle assembly 12 also includes the aforementioned clamp trigger 26, which is operably coupled with drive mechanism 80 such that, in use, when clamping trigger 26 is compressed towards battery assembly 18 (FIG. 1B), outer actuator tube 66 is slid about support tube 42 (in a distal-to-proximal or proximal-to-distal direction) to pivot jaw member 100 from the open position to the closed position in relation to blade member 32.

Battery assembly 18 is connected to a lower end of handle assembly 12 to define a fixed handgrip portion of handle assembly 12 and includes an outer housing 13. TAG 20 includes a generator 27 and an ultrasonic transducer (not explicitly shown). Generator 27 includes an outer housing 29. Other suitable configurations, both cordless and tethered, for providing power and ultrasonic energy, are also contemplated.

In general, in use, when battery assembly 18 and TAG 20 are attached to handle assembly 12 and waveguide 30, respectively, and ultrasonic surgical instrument 10 is activated, battery assembly 18 provides power to generator 27 of TAG 20 which, in turn, generates an AC signal to drive the ultrasonic transducer of TAG 20. The ultrasonic transducer, in turn, converts the AC signal into high frequency mechanical motion. This high frequency mechanical motion produced by the ultrasonic transducer is transmitted to blade member 32 via waveguide 30 for application of such ultrasonic energy to tissue adjacent to or clamped between blade member 32 and jaw member 100 of tool assembly 16 to treat the tissue.

Figure 3:
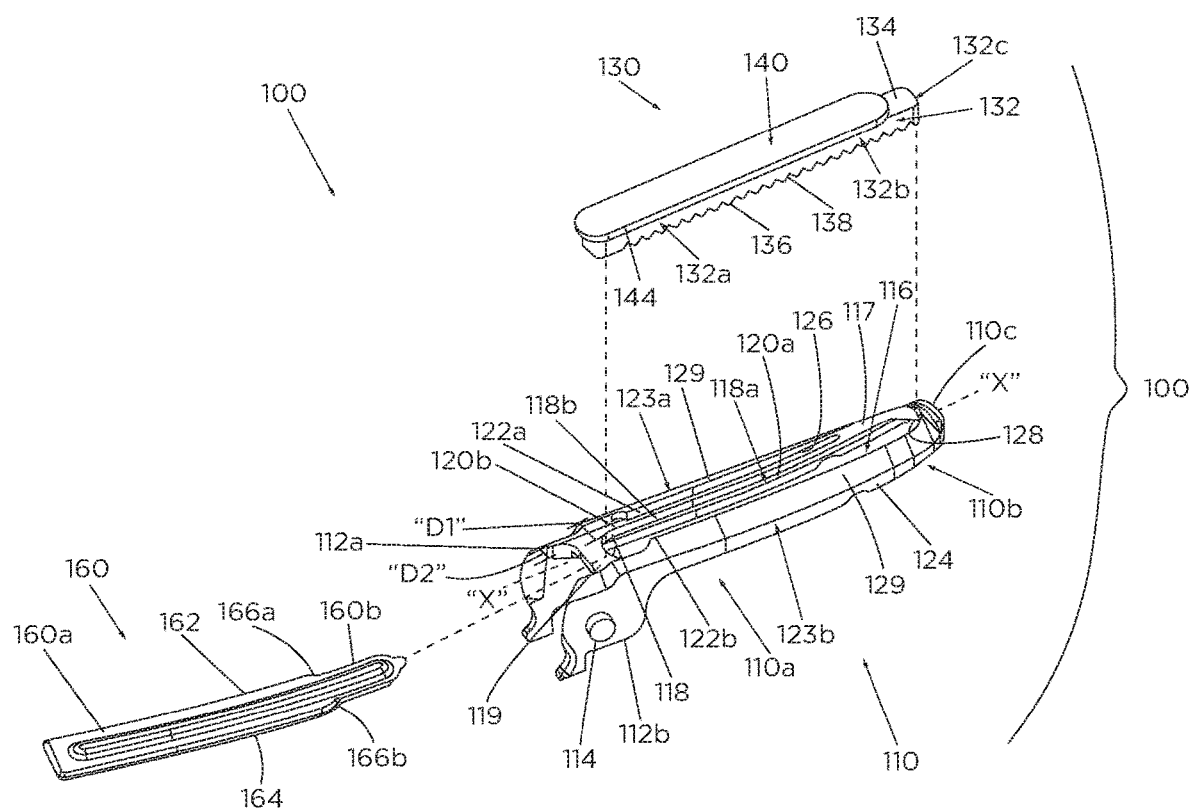
FIG. 3 is an exploded, perspective view of a jaw member for use with the ultrasonic surgical instrument of FIG. 1A.
Figure 4:
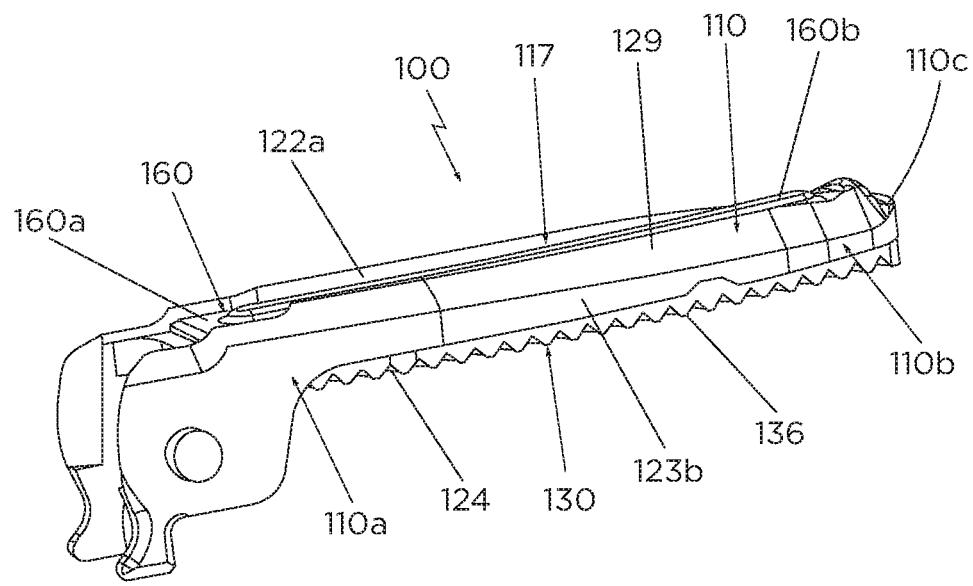
FIG. 4 is a perspective view of the jaw member of FIG. 3 in an assembled state.

With reference to FIGS. 3 and 4, an embodiment of a jaw member 100 configured for use with a surgical instrument, for example, ultrasonic surgical instrument 10 described above, is illustrated. Jaw member 100 generally includes a support base 110, a jaw liner 130, and an elongated plate 160. Support base 110 of jaw member 100 has a relatively rigid construction to provide integrity to jaw member 100 such that jaw member 100 can apply pressure to tissue when tool assembly 16 is in the clamped configuration (FIG. 1B). Support base 110 may be fabricated from a metal-containing material, for example, steel, or any other suitable material, and may be machined, stamped, metal injection molded, or formed via any other suitable process.

Support base 110 has a generally elongated configuration and defines a central longitudinal axis "X-X." It is contemplated that support base 110 may have a curvilinear configuration wherein at least a portion of support base 110 curves laterally off of central longitudinal axis "X-X," or a linear configuration along the central longitudinal axis "X-X." Support base 110 has a proximal portion 110a and a distal portion 110b. Proximal portion 110a of support base 110 has a pair of spaced-apart, proximally extending flanges 112a, 112b. Flanges 112a, 112b each have a connector, for example, a boss 114, configured for pivotable receipt in a correspondingly shaped recess (not explicitly shown) defined in spaced clamp support arms 52 (see FIG. 2) of ultrasonic surgical instrument 10. As such, when flanges 112a, 112b of support base 110 are coupled to spaced clamp support arms 52 of ultrasonic surgical instrument 10 (see FIG. 2), jaw member 100 is pivotable relative to blade member 32 of ultrasonic surgical instrument 10 to selectively clamp tissue between jaw member 100 and blade member 32 (see FIGS. 1A and 1B).

Support base 110 of jaw member 100 defines a cavity 116 therein that extends longitudinally along proximal and distal portions 110a, 110b thereof. Cavity 116 has closed distal and proximal ends and, thus, as detailed below, jaw insert 130 is inserted into support base 110 from an outer surface 129 of support base 110 (further from blade member 32 of ultrasonic surgical instrument 10 as compared to inner surface 124 of support base 110). This at least partial "drop-in" configuration facilitates assembly, particularly with respect to curved jaw members 100. Cavity 116 extends through inner surface 124 of support base 110, a thickness of support base 110, and outer surface 129 of support base 110. Cavity 116 is configured for receipt of jaw liner 130 and plate 160, as will be described in detail below.

Support base 110 includes first and second side walls 123a, 123b surrounding cavity 116 on either side thereof, and a stepped portion 118 extending from first and second side walls 123a, 123b inwardly into cavity 116. First and second side walls 123a, 123b are formed with one another at a rounded distal end portion 110c of support base 110. In some embodiments, first and second side walls 123a, 123b may be coupled to one another at the distal end portion 110c of support base 110 via a suitable connecting structure rather than being monolithically formed with one another.

Stepped portion 118 extends inwardly from first and second side walls 123a, 123b, as noted above. While each of the first and second side walls 123a, 123b has a stepped portion 118, for the purposes of brevity, only the stepped portion 118 extending from first side wall 123a will be described herein. Stepped portion 118 defines a first ledge 118a and a second ledge 118b, each of which having planar surfaces 120a, 120b oriented towards outer surface 129 of support base 110. First and second ledges 118a, 118b each extend generally longitudinally between the proximal and distal portions 110a, 110b of the support base 110 and are curvilinear similarly as support base 110.

The first ledge 118a of stepped portion 118 is disposed closer to inner surface 124 of support base 110 than second ledge 118b and protrudes from second ledge 118b further inwardly into cavity 116. In particular, first ledge 118a protrudes a first distance "D1" from the first side wall 123a and the second ledge 118b protrudes a second distance "D2" from the first side wall 123a, wherein "D1" is greater than "D2." As such, first ledge 118a protrudes a distance "D3=D1−D2" from second ledge 118b to support a projection 140 of jaw insert 130 thereon, as will be described below.

Second ledge 118b of stepped portion 118 includes a bridge 119 located at proximal portion 110a of support base 110 and which extends transversely between first and second side walls 123a, 123b of support base 110. Bridge 119 of second ledge 118b interconnects the second ledge 118b of first side wall 123a with the second ledge (not explicitly shown) of second side wall 123b thus forming one continuous second ledge 118b that spans the first and second side walls 123a, 123b. Bridge 119 further serves to close off and define the proximal end of cavity 116.

Outer surface 129 of support base 110 has a first extension or overhang 122a that extends from first side wall 123a of support base 110 over second ledge 118b to define an inner groove 126 between second ledge 118b and outer surface 129. Outer surface 129 of support base 110 has a second extension or overhang 122b that extends from second side wall 123b of support base 110 over the second ledge 118b of the stepped portion 118 on second side wall 123b. Inner groove 126 is dimensioned for slidable receipt of plate 160, in a proximal-to-distal direction, such that lateral sides 162, 164 of plate 160 are captured within the respective inner grooves 126 of first and second side walls 123a, 123b of support base 110. Distal portion 110b of support base 110 defines a longitudinally-extending notch 128 therein dimensioned for receipt of a distal portion of jaw liner 130.

With continued reference to FIGS. 3 and 4, jaw liner 130 of jaw member 100 is fabricated from a compliant material that allows blade member 32 of ultrasonic surgical instrument 10 (see FIG. 2) to vibrate while in contact therewith without causing damage to blade member 32 or other components of ultrasonic surgical instrument 10, and without compromising the hold on tissue grasped therebetween. Jaw liner 130 is configured to be situated in support base 110 such that blade member 32 makes contact with jaw liner 130 rather than support base 110 when tool assembly 16 is in the clamped condition (FIG. 1B). Jaw liner 130 may be fabricated from a plastic, for example, polytetrafluoroethylene, polyetheretherketone, perfluoroalkoxy, and/or fluorinated ethylene propylene. In some embodiments, jaw liner 130 may be fabricated from any suitable compliable material, for example, soft metals, rubbers, or the like. In other embodiments, jaw linear 130 may be fabricated from a metal.

Jaw liner 130 of jaw member 100 includes an elongate body 132 and a projection 140 disposed thereon. Elongate body 132 has a rectangular configuration and includes a proximal portion 132a and a distal portion 132b. In some embodiments, elongate body 132 may assume any suitable shape, such as, for example, triangular, square, elliptical, or the like. Elongate body 132 of jaw liner 130 is configured for receipt within cavity 116 of support base 110 and has an outer surface 134 and an inner tissue-contacting surface 136. Tissue-contacting surface 136 of jaw liner 130 has a plurality of teeth 138 disposed along a length of jaw liner 130. Teeth 138 have a trapezoidal shape, but it is contemplated that teeth 138 may assume and suitable shape that functions to aid in grasping or holding tissue between jaw member 100 and blade member 32 (FIG. 2).

Projection 140 of jaw liner 130 has an elliptical configuration and is disposed on outer surface 136 of elongate body 132. In some embodiments, projection 140 of jaw liner 130 may be integrally connected to outer surface 136 or a periphery of elongate body 132, or may be monolithically formed with outer surface 136 or the periphery of elongate body 132. Projection 140 has a peripheral edge 144 that extends laterally outward from opposing lateral sides of elongate body 132 and proximal portion 132a of elongate body 132, but is recessed proximally from a distal tip 132c of elongate body 132. As such, the peripheral edge 144 of projection 140 is configured to be disposed on planar surface 120a of first ledge 118a of support base 110 while distal tip 132c of elongate body 132 is configured to be disposed in notch 128 defined in distal portion 110b of support base 110.

With continued reference to FIGS. 3 and 4, elongated plate 160 of jaw member 100 has a proximal portion 160a and a distal portion 160b. Proximal portion 160a of plate 160 is configured to be disposed on second ledge 118b of support base 110 and to cover jaw liner 130 when jaw liner 130 is received within cavity 116 of support base 110. Plate 160 has opposing lateral sides 162, 164 that are dimensioned for receipt within inner grooves 126 of respective first and second side walls 123a, 123b of support base 110. Overhangs 122a, 122b of outer surface 129 of support base 110 maintain plate 160 on second ledge 118b of support base 110, thereby preventing plate 160 from falling out of an outwardly-facing opening 117 of cavity 116 of support base 110. Proximal portion 160a of plate 160 has a greater width than projection 140 of jaw liner 130 such that jaw liner 130 is dimensioned to be passed through outwardly-facing opening 117 of support base 110 while plate 160 is not.

To assemble or manufacture jaw member 100, jaw liner 130 is inserted into cavity 116 of support base 110 via outwardly-facing opening 117 thereof in an outer-to-inner direction (relative to outer and inner surfaces 129, 124 of support base 110) such that peripheral edge 144 of projection 140 of jaw liner 130 is positioned on first ledge 118a of support base 110. During such insertion, distal tip 132c of elongated body 132 of jaw liner 110 is tucked into notch 128 of support base 110. Tissue-contacting surface 136 of elongated body 132 of jaw liner 130 protrudes from inner surface 124 of support base 110 upon seating peripheral edge 144 of projection 140 of jaw liner 130 on first ledge 118a of support base 110. Peripheral edge 144 of projection 140 of jaw liner 130 abuts an inwardly-facing edge of distal end 110c of support base 110 to prevent jaw liner 130 from sliding distally relative to support base 110. Upon positioning jaw liner 130 in cavity 116 of support base 110, an under surface of peripheral edge 144 of projection 140 of jaw liner 130 abuts planar surface 120a of first ledge 118a of support base 110 to prevent jaw liner 130 from moving out of cavity 116 through inner surface 124 of support base 110, and opposing lateral sides of peripheral edge 144 of projection 140 of jaw liner 130 abut second ledges 118b of respective first and second side walls 123a, 123b to prevent side-to-side movement of jaw liner 130 within cavity 116 of support base 110. At this point, jaw liner 130 is substantially unconstrained from withdrawal from cavity 116 via outwardly-facing opening 117 thereof (other than the constraint of distal tip 132c of elongated body 132 of jaw liner 110 being tucked into notch 128 of support base 110).

With jaw liner 130 disposed within cavity 116 of support base 110, plate 160 is slid distally into cavity 116 of support base 110 to position the lateral sides 162, 164 of plate 160 within respective inner grooves 126 of first and second side walls 123a, 123b of support base 110. Distal movement of plate 160 is continued until shoulders 166a, 166b on respective lateral sides 162, 164 of plate 160 abut a distal end of inner grooves 126, and a proximal end of plate 160 is seated on bridge 119 of second ledge 118b. With plate 160 positioned over jaw liner 130 and captured between overhangs 122a, 122b of support base 110 and second ledge 118b of support base 110, plate 160 prevents jaw liner 130 from backing out of support base 110 through outwardly-facing opening 117 of support base 110. Plate 160, jaw liner 130, and support base 110 may be further configured such that plate 160 retains jaw liner 130 in position via compression-fit. In some embodiments, a jaw overmold (not shown) may be applied over plate 160 to aid in securing plate 160 to support base 110. Additionally or alternatively, plate 160 may be welded or otherwise permanently secured to support base 110 at select locations about the periphery of plate 160 or around the entire periphery thereof. Once jaw member 100 is manufactured, jaw member 100 may be pivotably connected to elongated body portion 14 (FIG. 2) of ultrasonic surgical instrument 10.

Figure 5:
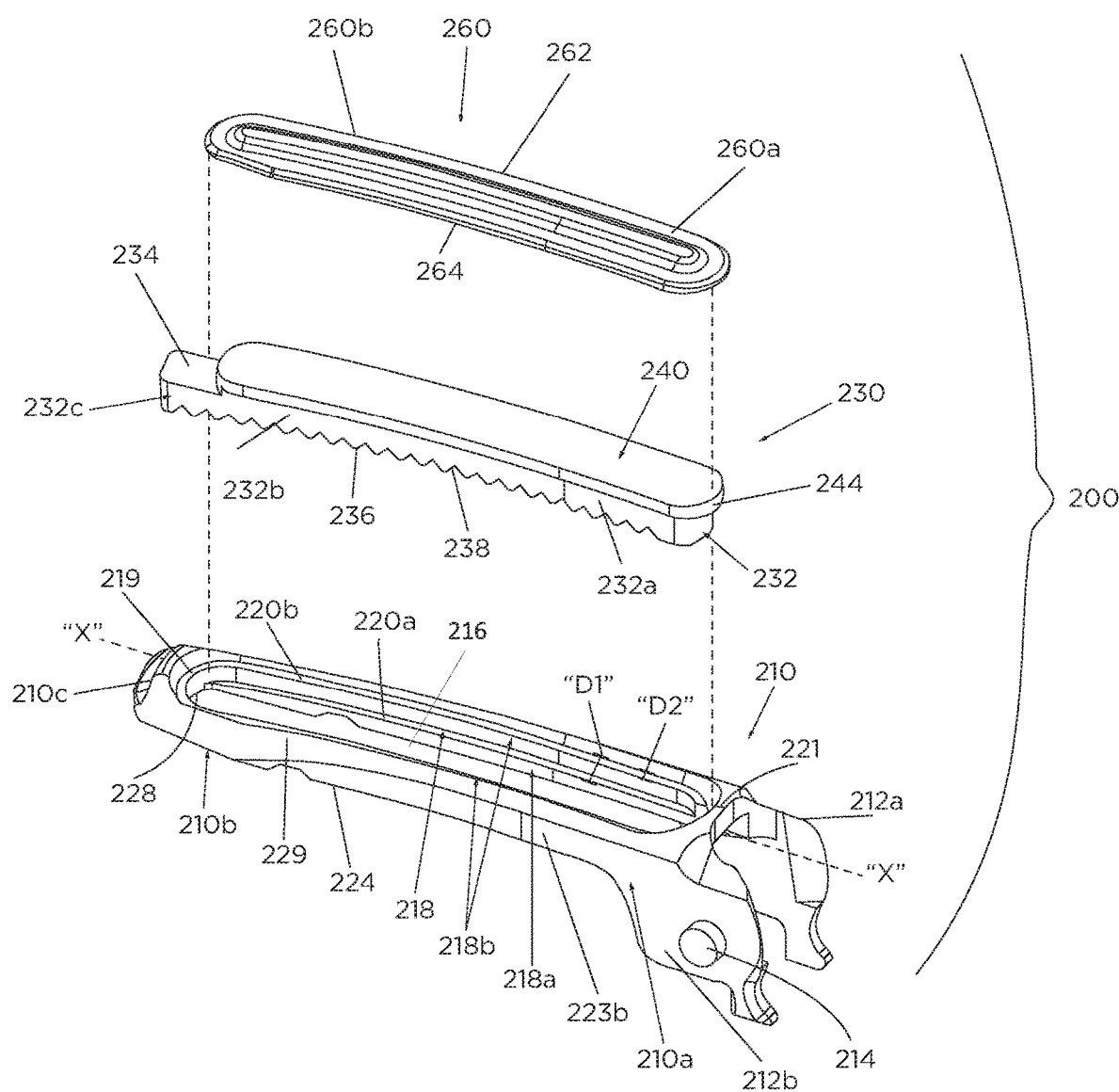
FIG. 5 is an exploded, perspective view of another jaw member for use with the ultrasonic surgical instrument of FIG. 1A.
Figure 6:
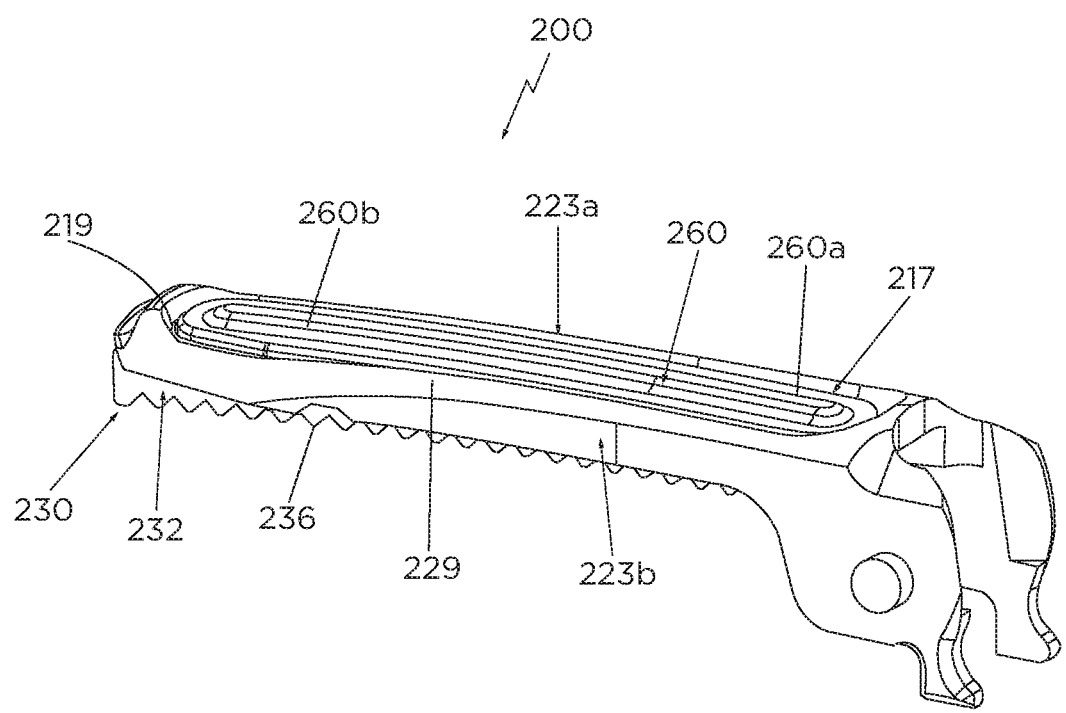
FIG. 6 is a perspective view of the jaw member of FIG. 5 in an assembled state.

With reference to FIGS. 5 and 6, another embodiment of a jaw member 200 configured for use with ultrasonic surgical instrument 10 is illustrated. Jaw member 200 generally includes a support base 210, a jaw liner 230, and an elongated plate 260.

Support base 210 of jaw member 200 has a relatively rigid construction to provide integrity to jaw member 200 such that jaw member 200 can apply pressure to tissue when tool assembly 16 is in the clamped configuration (FIG. 1B). Support base 210 may be fabricated from a metal-containing material, for example, steel, or any other suitable material, and may be machined, stamped, metal injection molded, or formed via any other suitable process.

Support base 210 has a generally elongated configuration and defines a central longitudinal axis "X-X." It is contemplated that support base 210 may have a curvilinear configuration wherein at least a portion of support base 210 curves laterally off of central longitudinal axis "X-X," or a linear configuration along the central longitudinal axis "X-X." Support base 210 has a proximal portion 210a and a distal portion 210b. Proximal portion 210a of support base 210 has a pair of spaced-apart, proximally extending flanges 212a, 212b. Flanges 212a, 212b each have a connector, for example, a boss 214 configured for pivotable receipt in a correspondingly shaped recess (not explicitly shown) defined in spaced clamp support arms 52 (see FIG. 2) of ultrasonic surgical instrument 10. As such, when flanges 212a, 212b of support base 210 are coupled to spaced clamp support arms 52 of ultrasonic surgical instrument 10 (see FIG. 2), jaw member 200 is pivotable relative to blade member 32 of ultrasonic surgical instrument 10 to selectively clamp tissue between jaw member 200 and blade member 32 (see FIGS. 1A and 1B).

Support base 210 of jaw member 200 defines a cavity 216 therein that extends longitudinally along proximal and distal portions 210a, 210b thereof. Cavity 216 has closed distal and proximal ends, such that jaw insert 230 is received in cavity 216 via outwardly-facing opening 217 defined in support base 210 from an outer surface 229 of support base 210 (further from blade member 32 of ultrasonic surgical instrument 10 as compared to an inner surface 224 of support base 210). This at least partial "drop-in" configuration facilitates assembly, particularly with respect to curved jaw member 100. Cavity 216 extends through inner surface 224 of support base 210, a thickness of support base 210, and outer surface 229 of support base 210. Cavity 216 is configured for receipt of jaw liner 230 and plate 260, as will be described in detail below.

Support base 210 includes first and second side walls 223a, 223b surrounding cavity 216 on either side thereof, and a stepped portion 218 extending from first and second side walls 223a, 223b inwardly into cavity 216. First and second side walls 223a, 223b are formed with one another at a rounded distal end portion 210c of support base 210 and are attached to one another via a transversely-extending bridge 221 located at proximal portion 210a of support base 210. In some embodiments, first and second side walls 223a, 223b may be coupled to one another, via a suitable connecting structure, rather than being monolithically formed with one another. Bridge serves to close off and define the proximal end of cavity 216.

Stepped portion 218 of support base 210 extends inwardly from first and second side walls 223a, 223b, as noted above. While each of the first and second side walls 223a, 223b of support base 210 has a stepped portion 218, for the purposes of brevity, only the stepped portion 218 extending from first side wall 223a will be described herein. Stepped portion 218 includes a first ledge 218a and a second ledge 218b, each of which having planar surfaces 220a, 220b that are oriented towards outer surface 229 of support base 210. First and second ledges 218a, 218b each extend generally longitudinally between the proximal and distal portions 210a, 210b of the support base 210 and are curvilinear similarly as support base 210.

First ledge 218a of stepped portion 218 is disposed closer to the inner surface 224 of support base 210 than second ledge 218b and protrudes from second ledge 218b further inwardly into cavity 216. In particular, first ledge 218a protrudes a first distance "D1" from the first side wall 223a and the second ledge 218b protrudes a second distance "D2" from the first side wall 223b, wherein "D1" is greater than "D2." As such, first ledge 218a protrudes a distance "D3=D1−D2" from second ledge 218b to support a projection 240 of jaw insert 230 thereon, as will be described below.

Second ledge 218b of stepped portion 218 includes an arcuate bridge 219 located at distal portion 210b of support base 210 and which extends between first and second side walls 223a, 223b of support base 210. Bridge 219 of second ledge 218b interconnects the second ledge 218b of first side wall 223a with the second ledge 218b of second side wall 223b. Bridge 219 further serves to close off and define the distal end of cavity 216. Distal portion 210b of support base 210 defines a longitudinally-extending notch 228 therein dimensioned for receipt of a distal portion of jaw liner 230.

With continued reference to FIGS. 5 and 6, jaw liner 230 of jaw member 200 is similar to jaw liner 130 described above with reference to FIGS. 3 and 4. In particular, jaw liner 230 of jaw member 200 includes an elongate body 232 and a projection 240 disposed thereon. Elongate body 232 has a rectangular configuration and includes a proximal portion 232a and a distal portion 232b. Elongate body 232 of jaw liner 230 is configured for receipt within cavity 216 of support base 210 and has an outer surface 234 and an inner tissue-contacting surface 236. Tissue-contacting surface 236 of jaw liner 230 has a plurality of teeth 238 disposed along a length of jaw liner 230.

Projection 240 of jaw liner 230 has an elliptical configuration and is disposed on outer surface 234 of elongate body 232. Projection 240 has a peripheral edge 244 that extends laterally outward from opposing lateral sides of elongate body 232 and proximal portion 232a of elongate body 232, but is recessed proximally from a distal tip 232c of elongate body 232. As such, the peripheral edge 244 of projection 240 is configured to be disposed on planar surface 220a of first ledge 218a of support base 210 while distal tip 232c of elongate body 232 is configured to be disposed within, e.g., tucked into, notch 228 defined in distal portion 210b of support base 210.

With continued reference to FIGS. 5 and 6, elongated plate 260 of jaw member 200 has a proximal portion 260a and a distal portion 260b. Each of proximal and distal portions 260a, 260b of plate 260 is configured to be disposed on second ledge 218b of support base 210 and to cover jaw liner 230 when jaw liner 230 is received within cavity 216 of support base 210. Instead of support base 230 having the overhangs 122a, 122b of support base 110 of FIGS. 3 and 4 to prevent plate 260 from falling out of outwardly-facing opening 217 of cavity 216, plate 260 is dimensioned for compression fit in cavity 216 of support base 210. Proximal portion 260a of plate 260 has a greater width than projection 240 of jaw liner 230 such that jaw liner 230 is dimensioned to be passed over second ledge 218b and onto first ledge 218a while plate 260 cannot pass over second ledge 218b.

To assemble or manufacture jaw member 200, jaw liner 230 is inserted into cavity 216 of support base 210 via outwardly-facing opening 217 thereof in an outer-to-inner direction (relative to outer and inner surfaces 229, 224 of support base 210) such that peripheral edge 244 of projection 240 of jaw liner 230 is positioned on first ledge 218a of support base 210. During such insertion, distal tip 232c of elongated body 232 of jaw liner 210 is tucked into notch 228 of support base 210. Tissue-contacting surface 236 of elongated body 232 of jaw liner 230 protrudes from inner surface 224 of support base 210 upon seating peripheral edge 244 of projection 240 of jaw liner 230 on first ledge 218a of support base 210. Peripheral edge 244 of projection 240 of jaw liner 230 abuts an inwardly-facing edge of distal end portion 210c of support base 210, thereby preventing jaw liner 230 from sliding distally relative to support base 210. First ledge 218a of support base 210 prevents jaw liner 230 from moving out of cavity 216 through inner surface 224 of support base 210.

Upon positioning jaw liner 230 in cavity 216 of support base 210, an under surface of peripheral edge 244 of projection 240 of jaw liner 230 abuts planar surface 220a of first ledge 218a of support base 210 to prevent jaw liner 230 from moving out of cavity 216 through inner surface 224 of support base 210, and opposing lateral sides of peripheral edge 244 of projection 240 of jaw liner 230 abut second ledges 218b of respective first and second side walls 223a, 223b to prevent side-to-side movement of jaw liner 230 within cavity 216 of support base 210. At this point, jaw liner 230 is substantially constrained from withdrawn from cavity 216 via outwardly-facing opening 217 thereof.

With jaw liner 230 disposed within cavity 216 of support base 210, plate 260 is inserted into cavity 216 of support base 210 via outer opening 217 of support base 210 to position lateral sides 262, 264 of plate 260 on second ledge 218b of support base 210. A threshold amount of a downward-oriented force is applied to plate 260 to form a compression fit between plate 260 and cavity 216 of support base 210. In some embodiments, instead of or in addition to forming a compression fit, an adhesive may be applied to an undersurface of plate 260 or planar surface 220b of second ledge 218b to secure plate 260 to support base 210. In other embodiments, a jaw overmold (not shown) may be applied over plate 260 to aid in securing plate 260 to support base 210.

With plate 260 positioned over jaw liner 230 and fixed to support base 210, plate 260 prevents jaw liner 230 from backing out of support base 210 through outer opening 217 of support base 210. Additionally, since cavity 216 of support base 210 is closed at its proximal end due to bridge 221 of support base 210, plate 260 and jaw insert 230 are each inhibited from backing out proximally from cavity 216 of support base 210. Additionally or alternatively, plate 260 may be welded or otherwise permanently secured to support base 210 at select locations about the periphery of plate 260 or around the entire periphery thereof. Once jaw member 200 is manufactured, jaw member 200 may be pivotably connected to elongated body portion 14 (FIG. 2) of ultrasonic surgical instrument 10.

Figure 7:
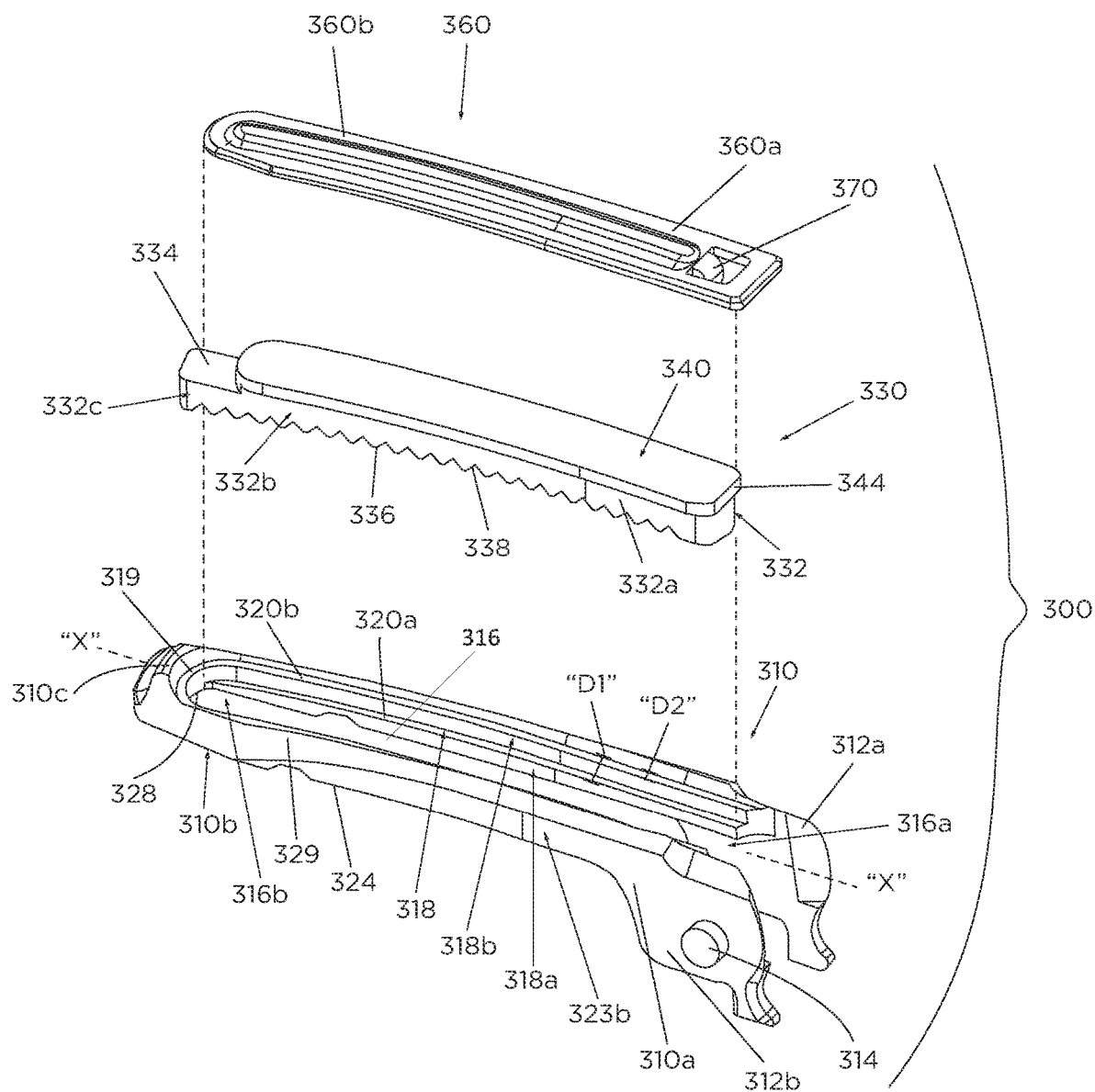
FIG. 7 is an exploded, perspective view of another jaw member for use with the ultrasonic surgical instrument of FIG. 1A.
Figure 8:
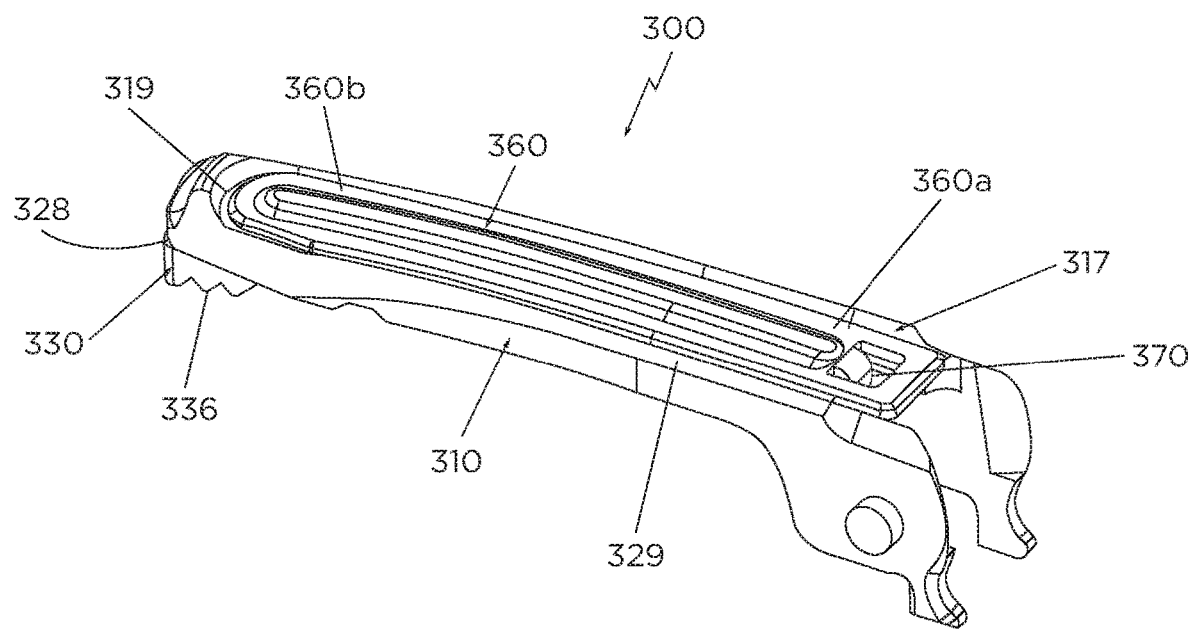
FIG. 8 is a perspective view of the jaw member of FIG. 7 in an assembled state.

With reference to FIGS. 7 and 8, another embodiment of a jaw member 300 configured for use with ultrasonic surgical instrument 10 is illustrated. Jaw member 300 generally includes a support base 310, a jaw liner 330, and an elongated plate 360.

Support base 310 of jaw member 300 has a relatively rigid construction to provide integrity to jaw member 300 such that jaw member 300 can apply pressure to tissue when tool assembly 16 is in the clamped configuration (FIG. 1B). Support base 310 may be fabricated from a metal-containing material, for example, steel, or any other suitable material, and may be machined, stamped, metal injection molded, or formed via any other suitable process.

Support base 310 has a generally elongated configuration and defines a central longitudinal axis "X-X." It is contemplated that support base 310 may have a curvilinear configuration wherein at least a portion of support base 310 curves laterally off of central longitudinal axis "X-X," or a linear configuration along the central longitudinal axis "X-X." Support base 310 has a proximal portion 310a and a distal portion 310b. Proximal portion 310a of support base 310 has a pair of spaced-apart, proximally extending flanges 312a, 312b. Flanges 312a, 312b each have a connector, for example, a boss 314 configured for pivotable receipt in a correspondingly shaped recess (not explicitly shown) defined in spaced clamp support arms 52 (see FIG. 2) of ultrasonic surgical instrument 10. As such, when flanges 312a, 312b of support base 310 are coupled to spaced clamp support arms 52 of ultrasonic surgical instrument 10 (see FIG. 2), jaw member 300 is pivotable relative to blade member 32 of ultrasonic surgical instrument 10 to selectively clamp tissue between jaw member 300 and blade member 32 (see FIGS. 1A and 1B).

Support base 310 of jaw member 300 defines a cavity or cavity 316 therein that extends longitudinally along proximal and distal portions 310a, 310b thereof. Cavity 316 has a closed distal end 316b and an open proximal end 316a. As detailed below, jaw insert 330 may be inserted into support base 310 from an outer surface 329 of support base 310 (further from blade member 32 of ultrasonic surgical instrument 10 as compared to an inner surface 324 of support base 310). This at least partial "drop-in" configuration facilitates assembly, particularly with respect to curved jaw member 100. Cavity 116 extends through inner surface 324 of support base 310, a thickness of support base 310, and outer surface 329 of support base 310. Cavity 316 is configured for receipt of jaw liner 330 and plate 360, as will be described in detail below.

Support base 310 includes first and second side walls 323a, 323b surrounding cavity 316 on either side thereof, and a stepped portion 318 extending from first and second side walls 323a, 323b inwardly into cavity 316. First and second side walls 323a, 323b are formed with one another at a rounded distal end portion 310c of support base 310 and transversely-spaced from one another at a proximal end of support base 310. In some embodiments, first and second side walls 323a, 323b may be coupled to one another, via a suitable connecting structure, rather than being monolithically formed with one another.

Stepped portion 318 extends inwardly from first and second side walls 323a, 323b, as noted above. While each of first and second side walls 323a, 323b of support base 310 has a stepped portion 318 extending therefrom, for the purposes of brevity, only the stepped portion 318 extending from first side wall 323a will be described herein. Stepped portion 318 defines a first ledge 318a and a second ledge 318b, each of which having planar surfaces 320a, 320b that are oriented towards outer surface 329 of support base 310. First and second ledges 318a, 318b each extend generally longitudinally between the proximal and distal portions 310a, 310b of the support base 310 and are curvilinear similarly as support base 310.

First ledge 318a of stepped portion 318 is disposed closer to the inner surface 324 of support base 310 than second ledge 318b and protrudes from second ledge 318b further inwardly into cavity 316. In particular, first ledge 318a protrudes a first distance "D1" from the first side wall 323a and the second ledge 318b protrudes a second distance "D2" from the first side wall 323a, wherein "D1" is greater than "D2." As such, first ledge 318a protrudes a distance "D3=D1−D2" from second ledge 318b to support a projection 340 of jaw insert 330 thereon, as will be described below.

Second ledge 318b includes an arcuate bridge 319 located at distal end portion 310c of support base 310 and which extends between first and second side walls 323a, 323b of support base 310. Bridge 319 of second ledge 318b interconnects the second ledge 318b of first side wall 323a with the second ledge 318b of second side wall 323b to support a distal portion 360b of plate 360 thereon. Distal portion 310b of support base 310 defines a longitudinally-extending notch 328 therein dimensioned for receipt of a distal portion of jaw liner 130. Bridge 319 further serves to close off and define the closed distal end of cavity 316.

With continued reference to FIGS. 7 and 8, jaw liner 330 of jaw member 300 is similar to jaw liners 130, 230 described above with reference to FIGS. 3-6. Jaw liner 330 of jaw member 300 includes an elongate body 332 and a projection 340 disposed thereon. Elongate body 332 has a rectangular configuration and includes a proximal portion 332a and a distal portion 332b. Elongate body 332 of jaw liner 330 is configured for receipt within cavity 316 of support base 310 and has an outer surface 334 and an inner tissue-contacting surface 336. Tissue-contacting surface 336 of jaw liner 330 has a plurality of teeth 338 disposed along a length of jaw liner 330.

Projection 340 of jaw liner 330 has an elliptical configuration and is disposed on outer surface 336 of elongate body 332. Projection 340 has a peripheral edge 344 that extends laterally outward from opposing lateral sides of elongate body 332 and proximal portion 332a of elongate body 332, but is recessed proximally from a distal tip 332c of elongate body 332. As such, the peripheral edge 344 of projection 340 is configured to be disposed on planar surface 320a of first ledge 318a of support base 310 while distal tip 332c of elongate body 332 is configured to be disposed in notch 328 defined in distal portion 310b of support base 310.

With continued reference to FIGS. 7 and 8, elongated plate 360 of jaw member 300 has a proximal portion 360a and a distal portion 360b. Each of proximal and distal portions 360a, 360b of plate 360 is configured to be disposed on second ledge 318b of support base 310 and to cover jaw liner 330 when jaw liner 330 is received within cavity 316 of support base 310. Instead of support base 310 having the overhangs 122a,122b of support base 130 of FIGS. 3 and 4 to prevent plate 360 from falling out of an outwardly-facing opening 317 of cavity 316, plate 360 is dimensioned for compression fit in cavity 316 of support base 310. Proximal portion 360a of plate 360 has a greater width than projection 340 of jaw liner 330 such that jaw liner 330 is dimensioned to be passed over second ledge 318b and onto first ledge 318a while plate 360 cannot pass over second ledge 318b.

Plate 360 is different from plate 260 of FIGS. 5 and 6 by having a tab 370 extending from proximal portion 360a thereof. Tab 370 extends substantially perpendicularly from an outer surface of plate 360. Tab 370 is configured to abut a proximal end of jaw liner 330 to prevent jaw liner 330 from sliding proximally out of open proximal end 316a of cavity 316.

To assemble or manufacture jaw member 300, jaw liner 330 is inserted into cavity 316 of support base 310 via outwardly-facing opening 317 thereof in an outer-to-inner direction (relative to outer and inner surfaces 329, 324 of support base 310) to position peripheral edge 344 of projection 340 of jaw liner 330 on first ledge 318a of support base 310. During such insertion, distal tip 332c of elongated body 323 of jaw liner 310 is tucked into notch 328 of support base 310. Tissue-contacting surface 336 of elongated body 332 of jaw liner 330 protrudes from inner surface 324 of support base 310 upon seating peripheral edge 344 of projection 340 of jaw liner 330 on first ledge 318a of support base 310. Peripheral edge 344 of projection 340 of jaw liner 330 abuts an inwardly-facing edge of distal end portion 310c of support base 310 to prevent jaw liner 330 from sliding distally relative to support base 310. Upon positioning jaw liner 330 in cavity 316 of support base 310, an under surface of peripheral edge 344 of projection 344 of jaw liner 330 abuts planar surface 320a of first ledge 318a of support base 310 to prevent jaw liner 330 from moving out of cavity 316 through inner surface 324 of support base 310, and opposing lateral sides of peripheral edge 344 of projection 340 of jaw liner 330 abut second ledges 318b of respective first and second side walls 323a, 323b to prevent side-to-side movement of jaw liner 130. At this point, jaw liner 330 is substantially unconstrained from withdrawal from cavity 316 via outwardly-facing opening 317 thereof.

With jaw liner 330 disposed within cavity 316 of support base 310, plate 360 is inserted into cavity 316 of support base 310 by moving plate 360 distally into cavity 316 via open proximal end 316a of cavity 316 of support base 310 to position the lateral sides of plate 360 on second ledge 318b of support base 310. Alternatively, plate 360 may be inserted into cavity 316 of support base 310 via outwardly-facing opening 317 thereof in an outer-to-inner direction rather than in a proximal-to-distal direction. A threshold amount of a distally-oriented force (alternatively an inner-oriented force) is applied to plate 360 to form a compression fit between plate 360 and cavity 316 of support base 310. In some embodiments, instead of or in addition to forming a compression fit, an adhesive may be applied to an under-surface of plate 360 or planar surface 320b of second ledge 320a to secure plate 360 to support base 310. In other embodiments, a jaw overmold (not shown) may be applied over plate 360 to aid in securing plate 360 to support base 310. Additionally or alternatively, plate 360 may be welded or otherwise permanently secured to support base 310 at select locations about the periphery of plate 360 or around the entire periphery thereof.

With plate 360 positioned over jaw liner 330 and fixed to support base 310, plate 360 prevents jaw liner 330 from backing out of support base 310 through outwardly-facing opening 317 of support base 310. Additionally, tab 370 of plate 360 is in abutment with proximal end of jaw liner 330 to prevent jaw liner 330 from backing out proximally from support base 310 via open proximal end 316a of cavity 316. Once jaw member 300 is assembled or manufactured, jaw member 300 may be pivotably connected to elongated body portion 14 (FIG. 2) of ultrasonic surgical instrument 10.

Figure 9:
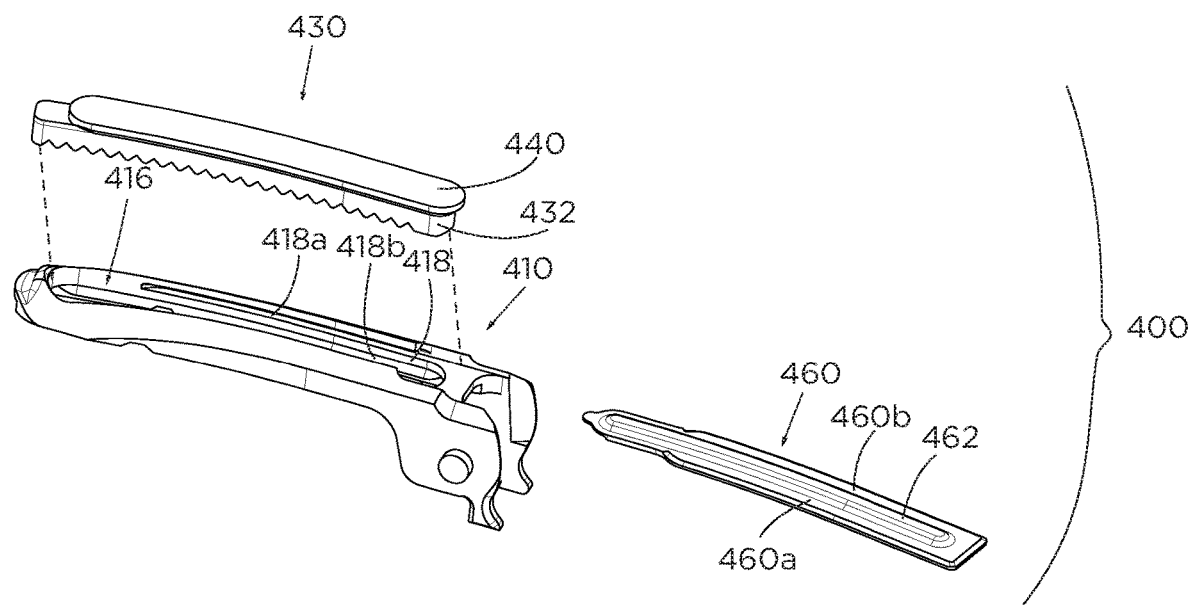
FIG. 9 is an exploded, perspective view of another jaw member for use with the ultrasonic surgical instrument of FIG. 1A.
Figure 10:
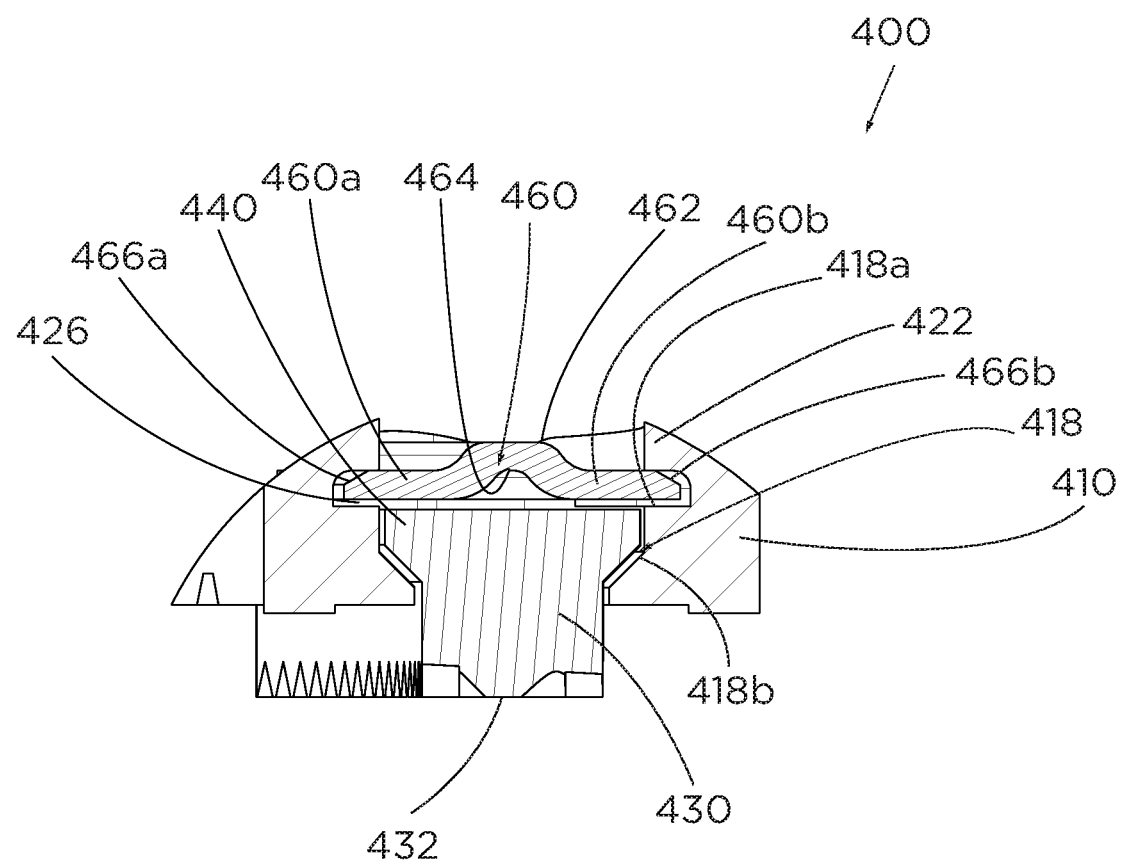
FIG. 10 is a transverse cross-sectional view of the jaw member of FIG. 9 in an assembled state.

With reference to FIGS. 9 and 10, another embodiment of a jaw member 400 is illustrated, similar to the jaw member 100 shown in FIGS. 3 and 4. Thus, only those features of jaw member 400 necessary to elucidate differences between jaw member 400 and jaw member 100 will be described.

Jaw member 400 generally includes a support base 410, a jaw liner 430, and an elongated plate 460. The support base 410 of jaw member 400 defines a cavity 416 therein dimensioned for receipt of jaw insert 430. Support base 410 has an extension or overhang 422 that defines an inner groove 426. Inner groove 426 is dimensioned for slidable receipt of plate 460, in a proximal-to-distal direction.

Support base 410 has a stepped portion 418 that defines a first ledge 418a and a second ledge 418b, similar to stepped portion 118 of jaw member 100 (FIGS. 3 and 4). However, instead of ledges 418a, 418b extending substantially parallel relative to one another as ledges 118a, 118b of support base 110 (FIGS. 3 and 4), second ledge 418b of support base 410 extends at an oblique angle relative to first ledge 418a of support base 410, which runs substantially parallel to a longitudinal axis defined by support base 410. As such, the cavity 416 of support base 410 has a wedge-shaped configuration as illustrated in FIG. 10. Additionally, instead of projection 440 of jaw liner 430 extending substantially perpendicularly from elongate body 432 of jaw liner 430 as with projection 110 of jaw liner 130 (FIGS. 3 and 4), projection 440 of jaw liner 430 flares outwardly from elongate body 432 of jaw liner 430 at an oblique angle, e.g., between about 10 and 80 degrees, and in some embodiments, between about 35 and 55 degrees. As such, projection 440 of jaw liner 430 is configured to complimentarily engage the slanted second ledge 418b of support base 410 when the jaw liner 430 is received within the cavity 416 of the support base 410, e.g., via a "drop-in" approach.

Plate 460 of jaw member 400 includes a spine 462 extending along a central longitudinal axis thereof. The spine 462 defines a longitudinally-extending gap 464 that divides plate 460 into two longitudinal half-sections 460a, 460b. The gap 464 allows half-sections 460a, 460b to flex toward one another about the spine 462 during insertion of plate 460 into cavity 416. As such, plate 460 may be assembled to support base 410 using a "drop-in" approach (similarly as with the assembly of jaw liner 430 with support base 410) rather than sliding plate 460 longitudinally into cavity 416. Plate 460 may define tapered lateral edges 466a, 466b on each of half-sections 460a, 460b to facilitate entry and/or exit of plate 460 from support base 410. In some embodiments, plate 460 may be assembled to support base 410 via sliding cover 460 longitudinally into groove 426, rather than being "dropped-in."

While several embodiments of the disclosure have been shown in the drawings, it is not intended that the disclosure be limited thereto, as it is intended that the disclosure be as broad in scope as the art will allow and that the specification be read likewise. Therefore, the above description should not be construed as limiting, but merely as exemplifications of particular embodiments. Those skilled in the art will envision other modifications within the scope and spirit of the claims appended hereto.

What is claimed is:

1. A jaw member for use with a surgical instrument, the jaw member comprising:
   a support base having a proximal portion configured to be pivotably coupled to a surgical instrument, and a distal portion, the support base defining a cavity extending longitudinally between the proximal and distal portions, the support base having a stepped portion formed within the cavity, the stepped portion defining a first ledge and a second ledge, wherein the cavity of the support base extends transversely through the support base from a tissue-oriented surface of the support base to an opposing outward-facing surface of the support base;
   a jaw liner including:
      an elongate body configured for receipt within the cavity of the support base; and
      a projection extending radially outward from a periphery of the elongate body and configured to be seated on the first ledge of the support base; and
   an elongated plate configured to be seated on the second ledge of the support base adjacent the jaw liner to secure the jaw liner relative to the support base.

2. The jaw member according to claim 1, wherein the stepped portion is disposed on both sides of the cavity and extends longitudinally therealong.

3. The jaw member according to claim 2, wherein the support base includes:
   a first side wall defining a first side of the cavity; and
   a second side wall defining a second side of the cavity, each of the first and second ledges of the support base protruding laterally from the first and second side walls inwardly into the cavity.

4. The jaw member according to claim 3, wherein the first ledge protrudes a first distance laterally from the first and second side walls and the second ledge protrudes a second distance laterally from the first and second side walls, the first distance being greater than the second distance.

5. The jaw member according to claim 1, wherein each of the first and second ledges of the support base extends along a length of the support base and is disposed within the cavity.

6. The jaw member according to claim 1, wherein the outward-facing surface extends over the second ledge such that the plate is configured to be captured between the outward-facing surface of the support base and the second ledge of the support base.

7. The jaw member according to claim 1, wherein the jaw liner has a tissue-contacting surface formed on the elongate body of the jaw liner.

8. The jaw member according to claim 7, wherein the tissue-contacting surface of the jaw liner is fabricated from plastic.

9. The jaw member according to claim 8, wherein the plastic is selected from the group consisting of polytetrafluoroethylene, polyetheretherketone, perfluoroalkoxy, and fluorinated ethylene propylene.

10. The jaw member according to claim 7, wherein the tissue-contacting surface has a plurality of teeth disposed along a length of the jaw liner.

11. The jaw member according to claim 7, wherein the tissue-contacting surface of the jaw liner projects from the tissue-oriented surface of the support base.

12. The jaw member according to claim 1, wherein the plate has a proximal portion and a tab extending from the proximal portion, the tab of the plate configured to abut a proximal portion of the projection of the jaw liner to prevent proximal movement of the jaw liner relative to the support base.

13. The jaw member according to claim 12, wherein the cavity of the support base is closed via a bridge inhibiting slidable insertion of the jaw liner into the cavity while permitting slidable insertion of the elongated plate into the cavity.

14. The jaw member according to claim 1, wherein the cavity of the support base has a closed proximal end such that proximal movement of the jaw liner relative to the support base is inhibited.

15. A surgical instrument, comprising:
   a handle assembly;
   an elongated body portion extending distally from the handle assembly; and
   a tool assembly operably coupled to the elongated body portion and including:
      a blade member; and
      a jaw member including:
         a support base having a proximal portion pivotably coupled to the elongated body portion, and a distal portion, the support base defining a cavity extending longitudinally between the proximal and distal portions, the support base having a stepped portion formed within the cavity, the stepped portion defining a first ledge and a second ledge, wherein the cavity of the support base extends transversely through the support base from a tissue-oriented surface of the support base to an opposing outward-facing surface of the support base;
         a jaw liner including:
            an elongate body received within the cavity of the support base; and
            a projection extending radially outward from a periphery of the elongate body and seated on the first ledge of the support base; and
         an elongated plate seated on the second ledge of the support base adjacent the jaw liner to secure the jaw liner relative to the support base, wherein the jaw member is movable relative to the blade member between an open position, in which the jaw liner of the jaw member is spaced from the blade member, and a closed position, in which the jaw liner of the jaw member is approximated relative to the blade member.

16. The surgical instrument according to claim 15, wherein the stepped portion is disposed on both sides of the cavity and extends longitudinally therealong.

17. The surgical instrument according to claim 16, wherein the support base includes:
 a first side wall defining a first side of the cavity; and
 a second side wall defining a second side of the cavity, each of the first and second ledges of the support base protruding laterally from the first and second side walls inwardly into the cavity.

18. The surgical instrument according to claim 17, wherein the first ledge protrudes a first distance laterally from the first and second side walls and the second ledge protrudes a second distance laterally from the first and second side walls, the first distance being greater than the second distance.

19. The surgical instrument according to claim 15, wherein each of the first and second ledges of the support base extends along a length of the support base and is disposed within the cavity.

20. The surgical instrument according to claim 15, wherein the outward-facing surface extends over the second ledge such that the plate is configured to be captured between the outward-facing surface of the support base and the second ledge of the support base.

* * * * *